United States Patent [19]
Mann

[11] Patent Number: 6,077,256
[45] Date of Patent: Jun. 20, 2000

[54] DELIVERY OF A COMPOSITION TO THE LUNG

[76] Inventor: Michael J. Mann, 42 Lincoln Rd., Newton, Mass. 02158

[21] Appl. No.: 09/167,291

[22] Filed: Oct. 6, 1998

[51] Int. Cl.[7] .................................................. A61M 31/00
[52] U.S. Cl. ............................ 604/500; 604/284; 604/94; 604/173; 604/28
[58] Field of Search ..................................... 604/500, 507, 604/508, 509, 510, 93, 96, 94, 264, 28, 173, 284, 529, 102

[56] References Cited

U.S. PATENT DOCUMENTS

| | | | |
|---|---|---|---|
| 3,995,623 | 12/1976 | Blake et al. | |
| 4,195,637 | 4/1980 | Gruntzig et al. | 604/509 |
| 4,248,224 | 2/1981 | Jones | 128/348 |
| 4,309,994 | 1/1982 | Grunwald | 128/348 |
| 4,712,551 | 12/1987 | Rayhanabad | 604/96 |
| 4,714,460 | 12/1987 | Calderon | 604/28 |
| 4,867,742 | 9/1989 | Calderon | 604/28 |
| 4,883,459 | 11/1989 | Calderon | 604/28 |
| 4,909,258 | 3/1990 | Kuntz et al. | 128/658 |
| 5,378,228 | 1/1995 | Schmalzried et al. | 604/8 |
| 5,413,581 | 5/1995 | Goy | 604/102 |
| 5,545,133 | 8/1996 | Burns et al. | 604/96 |
| 5,584,803 | 12/1996 | Stevens et al. | |
| 5,695,457 | 12/1997 | St. Goar et al. | 604/4 |
| 5,718,692 | 2/1998 | Schon et al. | 604/264 |
| 5,720,735 | 2/1998 | Dorros | 604/284 |
| 5,766,901 | 6/1998 | Mann et al. | |
| 5,823,996 | 10/1998 | Sparks | 604/96 |
| 5,833,645 | 11/1998 | Lieber et al. | 604/53 |
| 5,882,334 | 3/1999 | Sepetka et al. | 604/96 |
| 5,885,238 | 3/1999 | Stevens et al. | 604/4 |

OTHER PUBLICATIONS

Brown et al., "Percutaneous treatment of stenosed major aortopulmonary collaterals with balloon dilatation and stenting: what can be achieved?" Heart 79:24–28, 1998.

Feldman et al., "Technique of percutaneous transvenous mitral commissurotomy using the inoue balloon catheter," Cathet. Cardiovasc. Diagn. Suppl. 2:26–34, 1994.

Kinoshita et al., "Rapid increase in plasma endothelin concentrations during percutaneous balloon dilatation of the mitral valve in patients with mitral stenosis," Br. Heart J. 69(4):322–326, 1993.

Minchin et al., "Pharmacokinetics of doxorubicin in isolated lung of dogs and humans perfused in vivo," J. Pharm. and Exp. Ther. 229(1):193–198, 1984.

Moore et al., "Percutaneous use of stents to correct pulmonary artery stenosis in young children after cavopulmonary anastomosis," Am. Heart J. 130(6):1245–1249, 1995.

Nawata et al., "Sequential bilateral isolated lung perfusion in the rat: an experimental model," Ann. Thorac. Surg. 63:796–799, 1997.

Wang et al., "Prospective trial of combined hyperfractionated radiotherapy and brochinal arterial infusion of chemotherapy for locally advanced nonsmall cell lung cancer," Int. J. Rad. Onc. Biol. Phys. 34(2):309–313, 1996.

*Primary Examiner*—John G. Weiss
*Assistant Examiner*—Jeremy Thissell
*Attorney, Agent, or Firm*—Clark & Elbing LLP

[57] ABSTRACT

In general, the invention features methods for delivering a composition to the lung in a non-surgical, percutaneous approach by utilizing the pulmonary vasculature (i.e., the pulmonary arteries and veins).

Also disclosed are methods allowing for the lung-specific delivery of a composition, as well as a catheter that includes a deployable arm.

41 Claims, 6 Drawing Sheets

DELIVERY OF A COMPOSITION TO THE LUNG

BACKGROUND OF THE INVENTION

This invention relates to the delivery of compositions to the lung.

The lungs are large, multi-lobed organs located in the chest, with each lung (i.e., the right and left lung) composed of three main components: the bronchial tubes, the pulmonary arteries and veins, and the pulmonary parenchyma. The main blood inflow into the lungs is from the pulmonary trunk, which sends unoxygenated blood from the right ventricle of the heart. The pulmonary trunk divides into the left and right pulmonary arteries, which further branch to supply arteries to each of the lobes and segments of the left and right lung, respectively. Blood flowing through these arteries reaches the alveoli of the lungs where red blood cells are separated from air only by a thin membrane of alveolar-lining cells and endothelial cells of the capillaries. Here, oxygen is picked up and carbon dioxide discarded. Oxygenated blood then returns to the left atrium of the heart via the pulmonary veins.

Although there is only one pulmonary artery supplying each lung, there are typically two pulmonary veins per lung (i.e., two pulmonary veins for the right lung, and two pulmonary veins for the left lung). The schematic representation of the lungs shown in FIG. 1 depicts the major blood vessels supplying and draining the left and right lungs. FIG. 2 provides a schematic representation of the left and right pulmonary arteries and veins as they relate to the flow of blood through the heart.

Given their crucial role in the delivery of oxygen to cells throughout the body, any impairment of the functioning of one or both of the lungs through disease or damage is a serious health consideration. Diseases of the lung may be congenital, or may be induced or exacerbated by environmental factors. Air pollution, cigarette smoke, and other harmful air-borne agents (e.g., asbestos) can contribute to a variety of lung diseases including, without limitation, chronic airflow obstruction, pneumoconiosis, pneumonia, restrictive lung disease (also known as infiltrative lung disease), and primary or metastatic lung cancer. Hence, methods for facilitating delivery of a therapeutic composition (e.g., a drug) to the lung would be useful in treating, or at least alleviating the symptoms of, a lung disease.

SUMMARY OF THE INVENTION

In general, the invention features a method and apparatus for facilitating delivery of a composition to the lung via a non-surgical percutaneous approach that utilizes the pulmonary circulation.

Accordingly, in a first aspect, the invention features a method for delivering a composition to a lung that includes the steps of: (a) inserting a pulmonary artery catheter into a pulmonary artery supplying the lung via a first non-surgical percutaneous route, where the pulmonary artery catheter includes a deployable means for occluding the inserted pulmonary artery; (b) inserting a pulmonary vein catheter into a pulmonary vein draining the lung via a second non-surgical percutaneous route, where the pulmonary vein catheter includes a deployable means for occluding the inserted pulmonary vein; and (c) delivering the composition to the lung via at least one of the group consisting of the pulmonary artery catheter and the pulmonary vein catheter. In one embodiment, the composition delivered to the lung is collected by at least one of the group consisting of the pulmonary artery catheter and the pulmonary vein catheter, where the delivering catheter and the collecting catheter are different. In another embodiment, the delivering catheter is connected to the collecting catheter, where the composition collected by the collecting catheter is returned to the lung by the delivering catheter. Preferably, a number of the pulmonary veins drain the lung.

In another embodiment of the first aspect of the invention, the step (b) further includes inserting a number of the pulmonary vein catheters into the number of pulmonary veins draining the lung, where each of the pulmonary vein catheters includes a deployable means for occluding the inserted pulmonary vein, where the number of pulmonary vein catheters is equal to the number of pulmonary veins draining the lung, and where not more than one of the pulmonary vein catheters is inserted into one pulmonary vein. Preferably, the delivering step is via at least one of the group consisting of the pulmonary artery catheter and at least one of the pulmonary vein catheters. Preferably, the composition delivered to the lung is collected by at least one of the group consisting of the pulmonary artery catheter and at least one of the pulmonary vein catheters, where the delivering catheter and the collecting catheter are different. In another embodiment, the delivering catheter is connected to the collecting catheter, where the composition collected by the collecting catheter is returned to the lung by the delivering catheter.

In another embodiment of the first aspect of the invention, the pulmonary vein catheter further includes a number of deployable arms, where the number of deployable arms of the pulmonary vein catheter is equal to the number of pulmonary veins draining the lung minus one. In another embodiment, step (b) further includes inserting the number of deployable arms of the pulmonary vein catheter into the number of pulmonary veins draining the lung, where each of the deployable arms, when deployed, includes a deployable means for occluding the inserted pulmonary vein, and where not more than one of the deployable arms is inserted into one pulmonary vein. Preferably, the delivering step is via at least one of the group consisting of the pulmonary artery catheter, the pulmonary vein catheter, and at least one of the deployable arms of the pulmonary vein catheter. Preferably, the composition delivered to the lung is collected by at least one of the group consisting of the pulmonary artery catheter, the pulmonary vein catheter, and at least one of the deployable arms of the pulmonary vein catheter, where the delivering catheter and the collecting catheter are different. In another embodiment, the delivering catheter is connected to the collecting catheter, where the composition collected by the collecting catheter is returned to the lung by the delivering catheter.

In various embodiments of the first aspect of the invention, the pulmonary artery catheter or the pulmonary vein catheter is adapted for insertion via a conventional introducer sheathe, is adapted for insertion over a guidewire, is equipped with a gauge for monitoring pressure, is equipped with a flow meter for monitoring flow rate, is at least in part radio-opaque, or further includes a lumen that is in communication with a port located distal to the deployable occluding means. Preferably, the first non-surgical percutaneous route or the second non-surgical percutaneous route is visualized by a guidance technique selected from the group consisting of ultrasound guidance, radiographic guidance, and magnetic resonance guidance. In other embodiments, the first non-surgical percutaneous route is an intravenous approach and the second non-surgical percutaneous route is an intra-arterial approach.

In a second aspect, the invention features a method for delivering a drug to a lung that includes the steps of: (a) inserting a pulmonary catheter into a blood vessel of the lung via a non-surgical percutaneous route, where the pulmonary catheter includes a deployable means for occluding the inserted blood vessel; and (b) delivering the drug to the lung via the pulmonary catheter. In various embodiments, the non-surgical percutaneous route is visualized by a guidance technique selected from the group consisting of ultrasound guidance, radiographic guidance, and magnetic resonance guidance; and the non-surgical percutaneous route is selected from the group consisting of an intravenous approach and an intra-arterial approach. In other embodiments, the pulmonary catheter is adapted for insertion via a conventional introducer sheathe, is adapted for insertion over a guidewire, is equipped with a gauge for monitoring pressure, is equipped with a flow meter for monitoring flow rate, is at least in part radio-opaque, or further includes a lumen that is in communication with a port located distal to the deployable occluding means. The blood vessel of the lung may be a pulmonary artery supplying the lung, or may be a pulmonary vein draining the lung. Preferably, a number of pulmonary veins drain the lung.

In another embodiment of the second aspect of the invention, the pulmonary catheter further includes a number of catheters, where the number of catheters of the pulmonary catheter is equal to the number of pulmonary veins draining the lung. In another embodiment, the number of catheters of the pulmonary catheter is inserted into the number of the pulmonary veins such that not more than one catheter of the pulmonary catheter is inserted into one pulmonary vein, and where each of the catheters of the pulmonary catheter includes a deployable means for occluding the inserted pulmonary vein.

In yet another embodiment of the second aspect of the invention, the pulmonary catheter further includes a number of deployable arms, where the number of deployable arms of the pulmonary catheter is equal to the number of pulmonary veins draining the lung minus one. In another embodiment, the number of the deployable arms of the pulmonary catheter is inserted into the number of the pulmonary veins such that not more than one deployable arm of the pulmonary catheter is inserted into one pulmonary vein, and where each of the deployable arms of the pulmonary catheter, when deployed, includes a deployable means for occluding the inserted pulmonary vein.

In a third aspect, the invention features a catheter that includes a deployable means (e.g., a balloon) for occluding a blood vessel inserted with the catheter, a lumen that is in communication with a port located proximal to the deployable occluding means, and a deployable arm which is deployed by advancing the arm through the lumen and the port of the catheter. In various embodiments, the catheter further includes a second lumen that is in communication with a port located distal to the deployable occluding means, and the deployable arm, when deployed, includes a deployable means for occluding a blood vessel inserted with the deployable arm. Preferably, the deployable arm, when deployed, further includes a lumen that is in communication with a port located distal to the deployable occluding means of the deployable arm.

In various embodiments of the third aspect of the invention, the catheter is adapted for insertion via a conventional introducer sheathe, is adapted for insertion over a guidewire, is equipped with a gauge for monitoring pressure, is equipped with a flow meter for monitoring flow rate, or is at least in part radio-opaque.

By "drug" is meant a compound or composition that acts as a therapeutic, diagnostic, or preventive agent on a lung cell. A drug may produce a metabolic or phenotypic change in a lung cell, may alter the growth of a lung cell, may influence a lung cell's interactions with other cells, may influence the genetic make-up or genetic activity of a lung cell, or may result in the death of a lung cell. For the purposes of the invention, a drug specifically excludes any compound or composition administered at a dosage or delivered at a concentration sufficient to facilitate blood flow though the pulmonary vasculature (e.g., heparin).

By "lung" is meant either the right lung, the left lung, or both of the right and left lungs.

By "pulmonary artery" is meant either the right pulmonary artery, the left pulmonary artery, or the main pulmonary trunk.

By "lung cell" is meant a cell that is located in the lung. Lung cells include, without limitation, cells of the lung parenchyma, cancerous lung cells, vascular endothelial cells lining the pulmonary blood vessels, and any cells of any origin which happen to reside in the lung (e.g., metastatic cancer cells of ectopic origin).

By "proximal" is meant that a catheter feature is closer to the person administering the catheter than a reference object. For example, a feature (e.g., a port) located proximal to a reference object (e.g., an occluding device) is closer to the person administering the catheter than the reference object. Hence, the feature is located between the person administering the catheter and the reference object.

By "distal" is meant that a catheter feature is more distant from the person administering the catheter than a reference object. For example, a feature (e.g., a port) located distal to a reference object (e.g., an occluding device) is farther from the person administering the catheter than the reference object. Hence, the reference object is located between the person administering the catheter and the feature.

The invention described herein provides methods for delivering a composition to the lung via the pulmonary circulation by using a non-surgical, percutaneous approach. The invention also features methods for the lung-specific delivery of a composition. By localizing the delivery of a composition to the lung, a higher concentration of a composition (e.g., a drug) may be administered than would have been administered systemically due to, for example, toxicity of the composition to other areas of the body (e.g., the bone marrow compartment).

Other features and advantages of the invention will be apparent from the following detailed description thereof, and from the claims.

BRIEF DESCRIPTION OF THE DRAWINGS

In FIG. 5B, a cross section is shown of the pulmonary vein catheter consisting of one catheter where the deployable arm of the catheter is a second catheter that is deployed by advancing the second catheter through the second lumen (14) of the pulmonary vein catheter. The second catheter is positioned in the second of the pulmonary veins draining the right lung, and includes a lumen (16) that is in communication with a port (17) located at the distal end of the second catheter, and a deployable occluding device (15), shown here in the deployed position.

DETAILED DESCRIPTION

Figure 1:
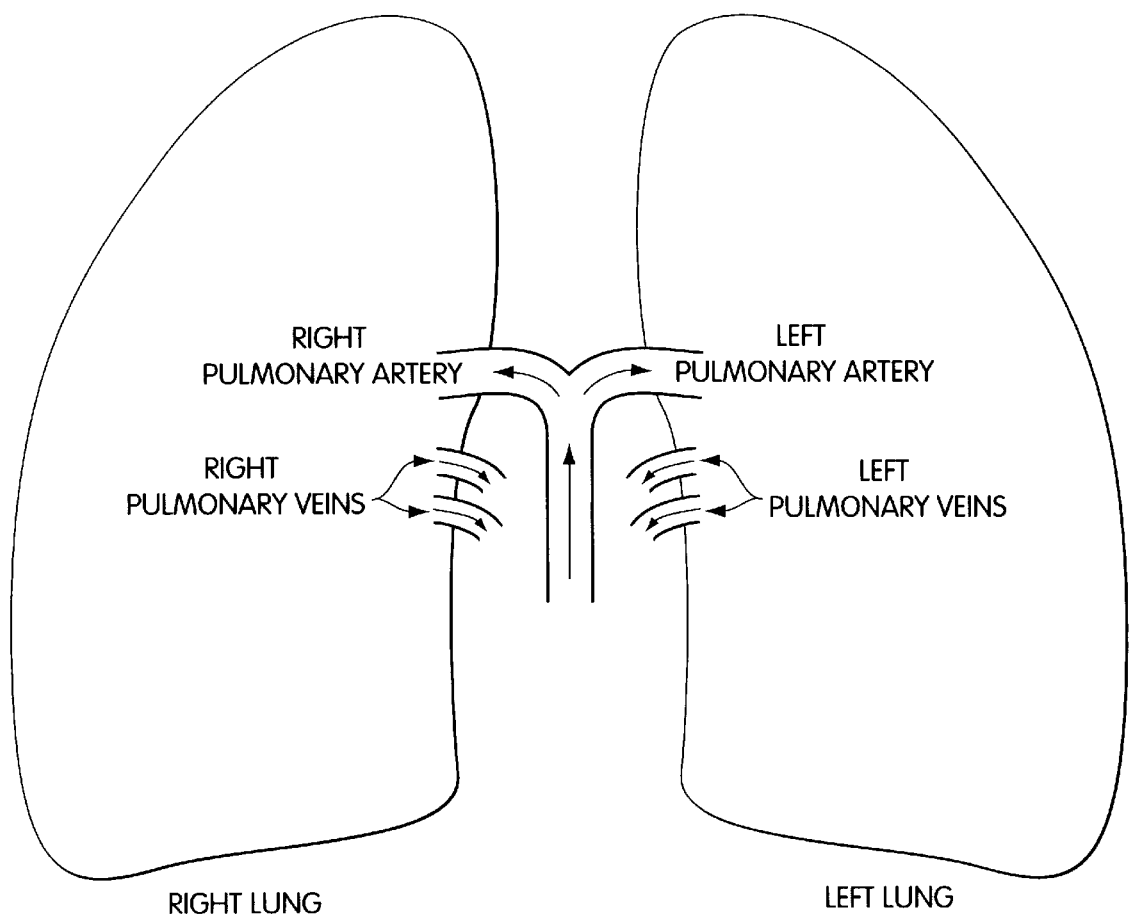
FIG. 1 is a schematic diagram of the major blood vessels of the lungs. Direction of blood flow is depicted with arrows. Blood flows into the lung via the pulmonary artery, and exits via the pulmonary veins.
Figure 2:
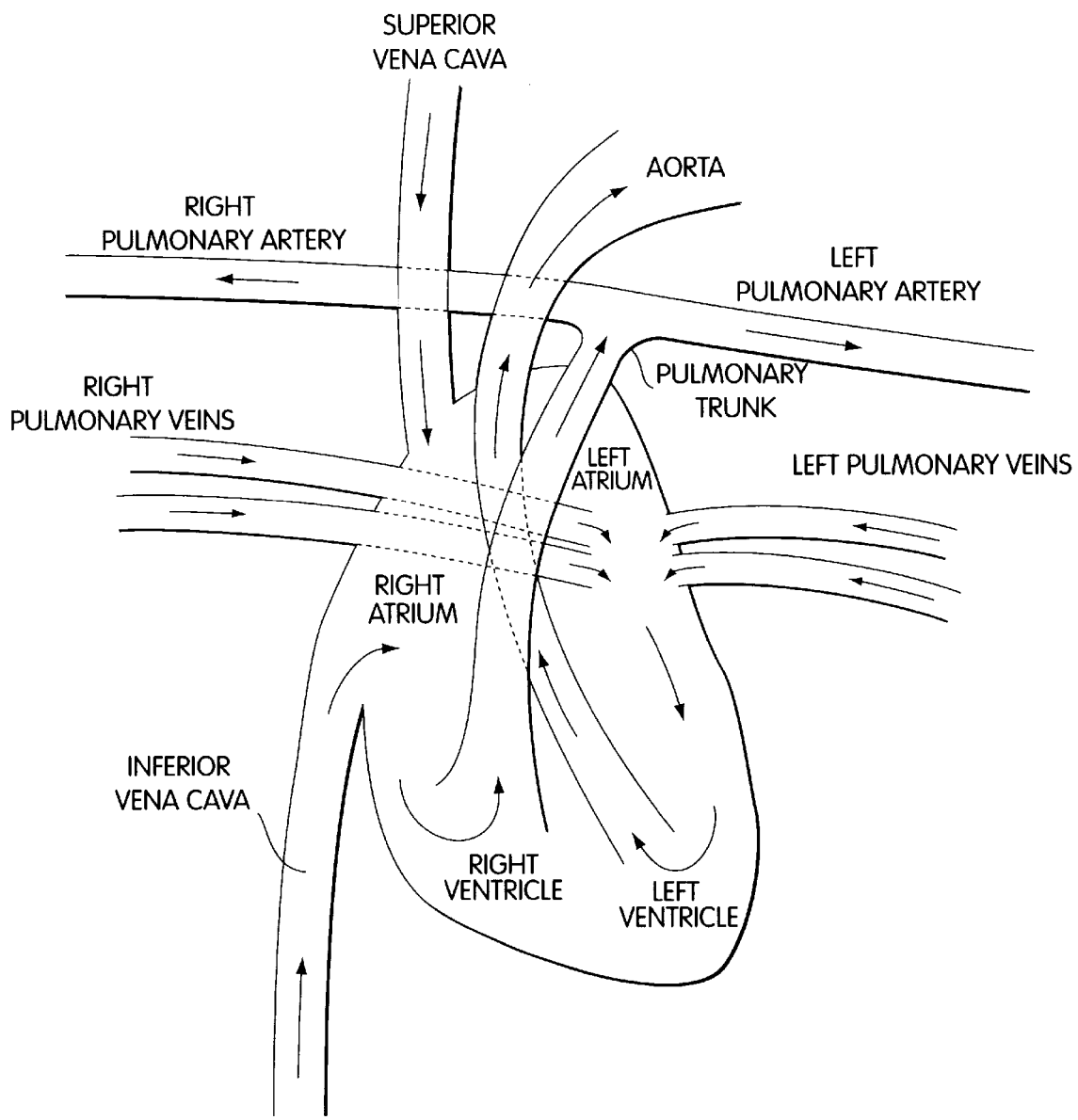
FIG. 2 is a schematic diagram of blood flow through the heart. Direction of blood flow is depicted with arrows. Unoxygenated blood enters the right atrium of the heart from the body via the superior and inferior vena cava. From the right atrium, blood then flows through the right ventricle into the pulmonary trunk. The pulmonary trunk divides into the left and right pulmonary arteries, which carry blood into the left and right lung, respectively. Oxygenated blood returns from the lungs via the left and right pulmonary veins, which enter the left atrium. The left atrium blood then flows into the left ventricle, and exits the heart via the aorta.

Utilizing a non-surgical percutaneous approach that employs the major blood vessels of the lung (e.g., the pulmonary arteries and veins), the present invention features delivery of a composition to the cells of the lung. In one variation of the delivery methods of the invention, a method is described for administering a composition (e.g., a drug) to one of the right or left lung, or both via a catheter that is placed via a percutaneous approach into either the pulmonary artery supplying the targeted lung(s) or into the pulmonary veins draining the targeted lung(s).

In addition, a method is described that allows the complete percutaneous, minimally invasive, non-surgical isolation of a lung for the delivery of a composition. By employing the multi-catheter apparatus described below, a composition may be delivered to cells of the right or left lung, or both lungs, in isolation, thereby preventing delivery of the composition to any non-lung cells. With this method, a therapeutic composition (e.g., a chemotherapeutic agent) found to treat or alleviate the symptoms of a lung disease (e.g., cancer) may be delivered in very high concentrations to the affected area without consideration for the effects of the composition on surrounding, unaffected non-lung tissue (e.g., the gastro-intestinal tract).

The methods of the invention allow for the control of pressure and flow rate of the administered composition by simply regulating the flow rate at which a composition is added to the lung. Hence, the pressure and flow rate of an administered composition may be manipulated as desired for enhanced delivery to the cells of the lung and/or enhanced uptake by cells of the lung.

In one variation of the methods of the invention, a composition will be administered to only one of the left or right lungs at any one point in time. Hence, a catheter (i.e., a pulmonary artery catheter) will be placed through the right atrium, across the tricuspid valve, through the right ventricle, across the pulmonary valve, into the pulmonary trunk, and into one of either the left or right pulmonary arteries. Likewise, a pulmonary vein catheter targeting only one set (i.e., left or right) of pulmonary veins is placed through the aorta, across the aortic valve, through the left ventricle, across the mitral valve, through the left atrium, and into the corresponding left or right pulmonary veins. The diameters of the pulmonary artery and pulmonary vein catheters, while variable, are selected so that blood may flow around the catheters, thereby allowing the heart to function with the non-isolated lung (i.e., the lung to which a composition is not being delivered).

In another variation of the methods of the invention, catheters are placed in the main pulmonary artery trunk (or both of the right and left pulmonary arteries) and both the right and left sets of pulmonary veins for perfusion of both lungs while the patient is placed on cardiopulmonary bypass. This bypass may be achieved, for example, via femoral artery and vein canulation, with arrest of the heart achieved via infusion of a cardioplegic solution administered through the coronary arteries using a percutaneous aortic root infusion balloon catheter (see, for example, Stevens et al., U.S. Pat. No. 5,584,803).

Apparatus for Delivering A Composition to the Lung

An apparatus for delivering a composition to lung cells has been developed which utilizes a series of catheters, one of which targets the pulmonary veins draining one of the right or left lung, and another of which targets the pulmonary artery supplying that lung.

A catheter may be introduced into the left or right pulmonary artery using a percutaneous approach, for example, via an intravenous approach through the right atrium and ventricle into the pulmonary trunk and, hence, into either the left or right pulmonary artery. Likewise, a catheter may be introduced into the left or right pulmonary veins using a percutaneous approach, for example, via an arterial access through the left ventricle, into the left atrium, and then into the either the left or right pulmonary veins.

A) The pulmonary artery catheter

A catheter is introduced into the either the left or right pulmonary artery. The pulmonary artery catheter is introduced in an intravenous approach through the right atrium, across the tricuspid valve (located between the right atrium and right ventricle), into the right ventricle, across the pulmonary valve, into the pulmonary trunk, and into either the left or right pulmonary artery. A pulmonary artery catheter may serve to either deliver a composition to the left or right lung, or to collect a composition from the left or right lung that is delivered by a pulmonary vein catheter. In its role as a collector or deliverer of a composition to or from the lung, the pulmonary artery catheter has a lumen that is in communication with a port located distal to a deployable occluding device (e.g., a balloon) for lodging the catheter within the pulmonary artery.

Alternatively, the pulmonary artery catheter may be employed to prevent a composition delivered by a pulmonary vein catheter from returning to the heart via the pulmonary artery and pulmonary trunk. In this instance, the pulmonary artery catheter has a deployable occluding device (e.g., a balloon) for lodging the catheter within the pulmonary artery, and may or may not additionally have a lumen that is in communication with a port located distal to the deployable occluding device.

Figure 3:
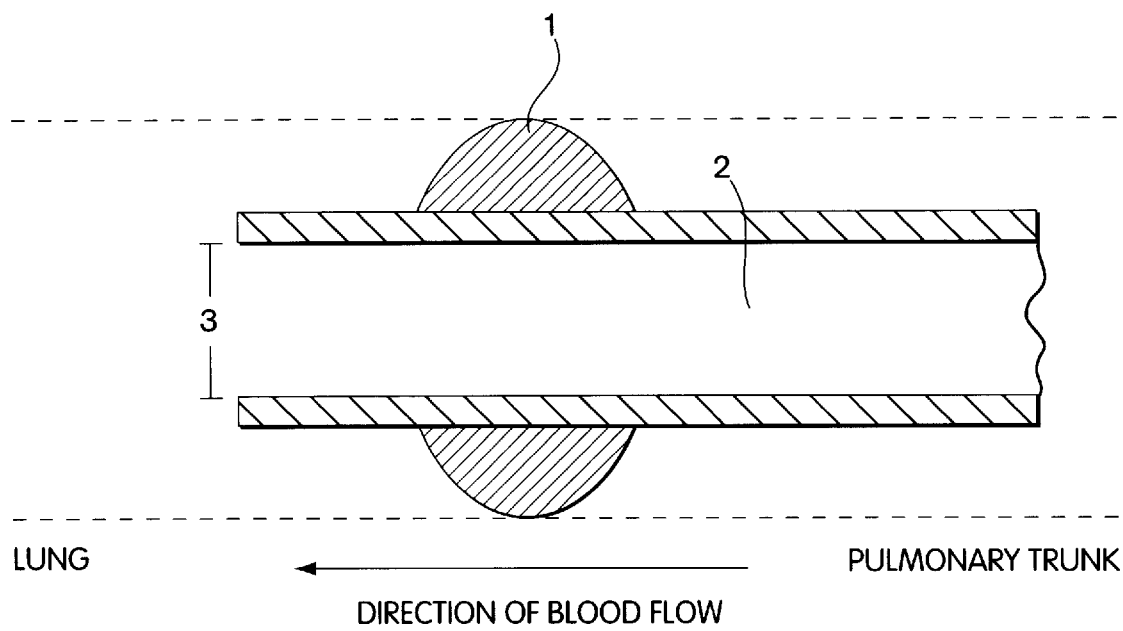
FIG. 3 is a schematic representation of a horizontal cross section of a pulmonary artery catheter useful in the invention. The pulmonary artery depicted in this figure may be either the left or the right pulmonary artery. Note that the deployable occluding device (1), denoted as a hatched section, is in the deployed position, firmly lodging the catheter against the wall of the pulmonary artery, which is denoted as a dotted line. Additionally note that the direction of the flow of blood in the pulmonary artery is from right to left in this figure.

A schematic diagram of a catheter that may be inserted into either the right or left pulmonary artery is provided in FIG. 3. The pulmonary artery catheter has a deployable occluding device (1), such as a balloon, that is mounted on the catheter. When deployed (the configuration depicted in FIG. 3), the deployable occluding device (1) occludes the pulmonary artery, thereby halting blood flow in the pulmonary artery. The deployed occluding device may additionally serve to prevent any undesired backflow of the composition being added to the lung into a region of the pulmonary artery located distal the occluding device (i.e., to the right of the occluding device (1) shown in FIG. 3). The pulmonary artery catheter is further equipped with a lumen (2) for delivery of a fluid via a port (3) proximal to the occluding device (1) through which a composition can be delivered either in solution or suspension.

Where both lungs are targeted simultaneously, a pulmonary artery catheter may be placed into the main pulmonary trunk. Less preferably, in a method to simultaneously deliver a composition to both lungs, two pulmonary artery catheters may be employed where each of the pulmonary artery catheters is placed into either the right or left pulmonary artery.

B) The pulmonary vein catheter

A pulmonary vein catheter is introduced into the pulmonary veins draining the left or right lung. The pulmonary vein catheter may be introduced via an arterial access through the left ventricle, across the mitral valve (located between the left atrium and left ventricle), into the left atrium, and then into either the left or right set of pulmonary veins.

The pulmonary vein catheter may be employed to allow the isolation of return flow of a composition from the pulmonary veins draining the targeted lung. Hence, the pulmonary vein catheter may be used to collect a composition draining the targeted lung that is delivered by a pulmonary artery catheter. Conversely, the pulmonary vein catheter may be used to deliver a composition to a targeted lung. In its role as a delivery or collecting catheter, the pulmonary vein catheter has a lumen that is in communication with a port located distal to a deployable occluding device (e.g., a balloon) for lodging the catheter within the pulmonary veins.

The pulmonary vein catheter may also be employed to simply prevent a composition administered to the lung from returning to the heart via the pulmonary veins. In this instance, the pulmonary vein catheter has a deployable occluding device (e.g., a balloon) for lodging the catheter within the pulmonary vein, and may or may not additionally have a lumen that is in communication with a port located distal to the deployable occluding device.

i) A pulmonary vein catheter consisting of two or more catheters

The pulmonary vein catheter may consist of more than one catheter, where each of the catheters targets one of the set of pulmonary veins draining either the right or left lung. For example, since most individuals have two pulmonary veins draining each lung, to target the left lung, two catheters are introduced into each of the two left pulmonary veins. A two-catheter example of a pulmonary vein catheter introduced into the left pulmonary veins is depicted on FIG. 4. Note that each of the two catheters has a deployable occluding device (4 and 5 in FIG. 4) for lodging each catheter within a left pulmonary vein. Each of the two catheters depicted in FIG. 4 also has a lumen (6 and 7) that is in communication with a port (8 and 9) located distal to the deployable occluding device.

In the case of individuals having, for example, more than two left pulmonary veins draining the left lung, the pulmonary vein catheter consisting of two or more catheters employed will consist of a set of three or more catheters, each of which is introduced into each of the left pulmonary veins present in that individual.

ii) A pulmonary vein catheter consisting of only one catheter

In another variation of the pulmonary vein catheter, again, in the example of an individual having two pulmonary veins draining each lung, the pulmonary vein catheter consists of only one catheter having a deployable arm, where the deployable arm, when deployed, has a deployable occluding device and may also have a lumen that is in communication with a port located distal to that deployable occluding device. When positioned in the left atrium at the point where the desired pulmonary veins (e.g., the right pulmonary veins) drain into the left atrium, the deployable arm of the catheter is deployed, such that the deployed arm is positioned in the first of the two left pulmonary veins, and the distal end of the catheter is positioned in the second of the two right pulmonary veins.

Figure 5A:
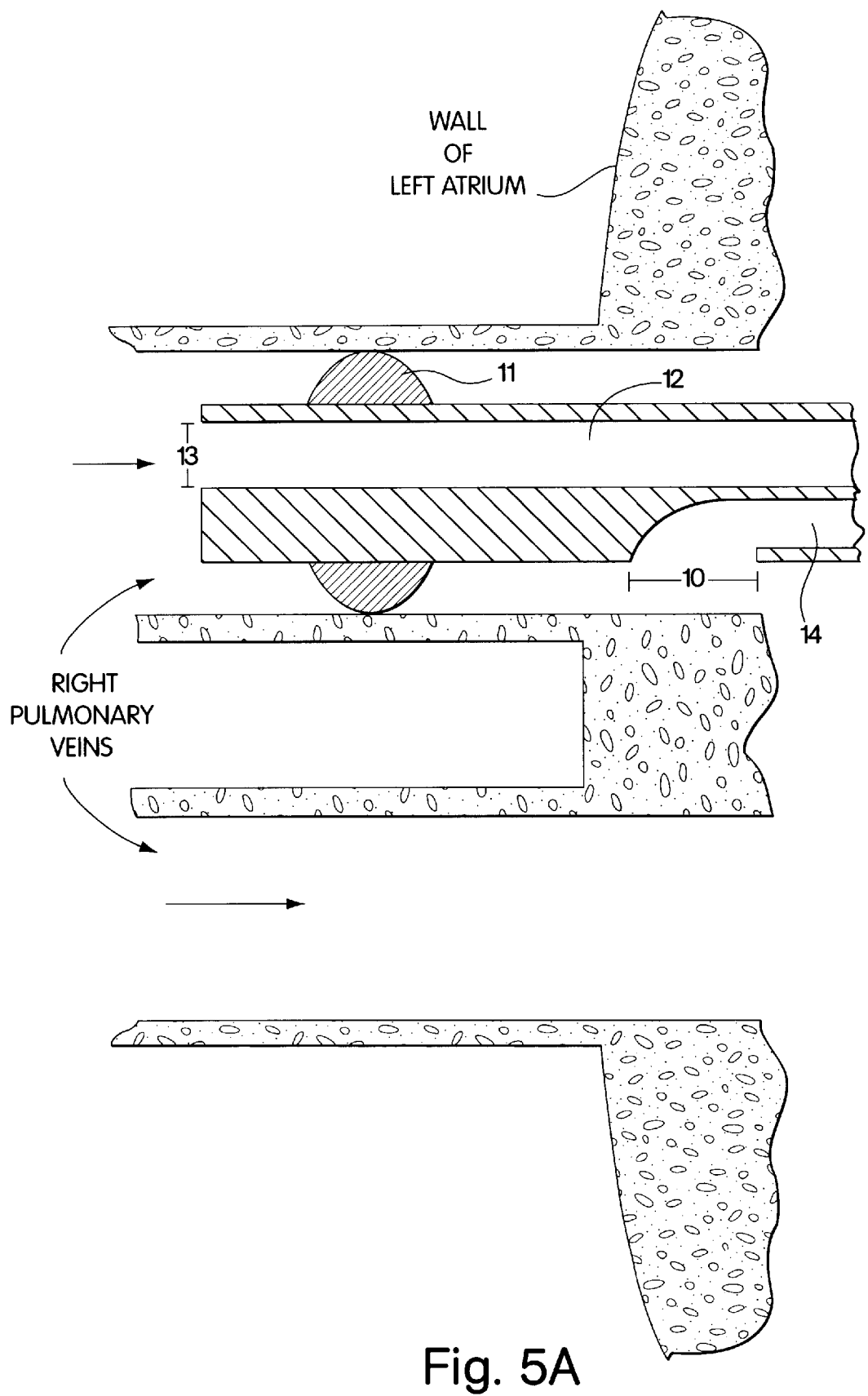
FIGS. 5A and 5B are schematic diagrams of a horizontal cross section of a pulmonary vein catheter that consists of only one catheter having a deployable arm and two lumens, where the first lumen (12) is in communication with a port located at the distal end of the catheter (13), and the second lumen (14) is in communication with a port (10) located proximal to the deployable occluding device (11) of the catheter. In these figures, the pulmonary veins depicted are draining the right lung. Shown in FIG. 5A is a horizontal cross section of the catheter with the deployable occluding device (11) shown in the deployed position, thus firmly lodging the distal end of the catheter against the walls of one of the two right pulmonary veins.
Figure 5B:
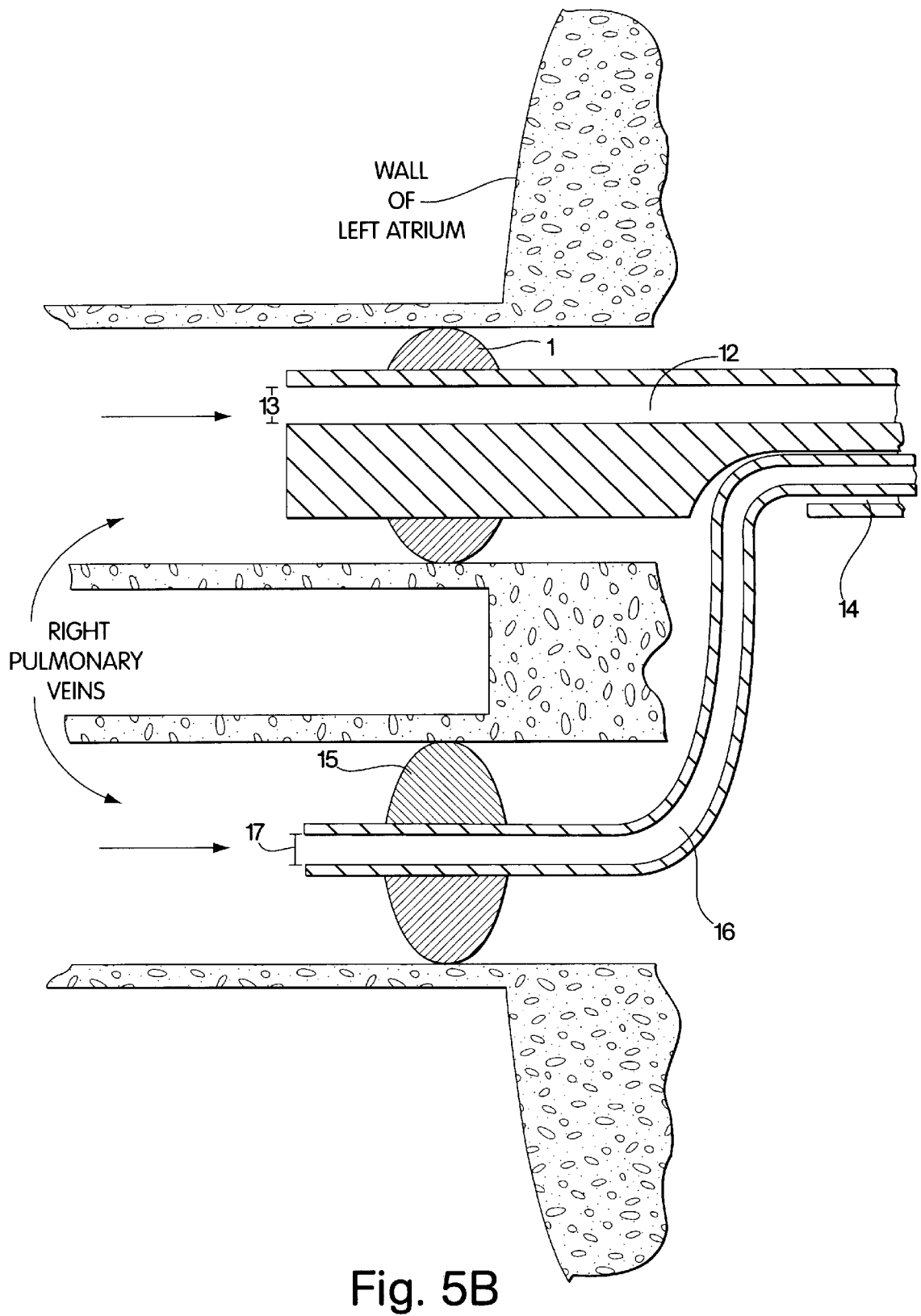

A schematic diagram of such a pulmonary vein catheter is shown on FIGS. 5A and 5B. This catheter has two lumens (12 and 14 in FIGS. 5A and 5B), each in communication with a port (13 and 10 in FIG. 5A) located either at the distal end of the catheter (port 13) or proximal to the deployable occluding device (11) of the catheter (port 10). The port (10) that is in communication with the second lumen (14) may also include a one-way valve to prevent flow of blood into the lumen (14) as the catheter is advanced into the pulmonary vein. Once the distal end of the catheter is correctly positioned in the first right pulmonary vein, the deployable arm of the pulmonary vein catheter, consisting of a second balloon catheter having an external diameter (when the balloon is not deployed) that is smaller than the diameter of lumen (14), is deployed by advancing the second catheter through the second lumen (14) and positioning the second catheter into the second right pulmonary vein (FIG. 5B). The second catheter of this pulmonary vein catheter has a deployable occluding device (15) and may have a lumen (16) that is in communication with a port (17) located at the distal end of the second catheter. Once positioned in the second right pulmonary vein, the deployable occluding device (15) of the second catheter is deployed, thus occluding the flow of blood in the second pulmonary vein. Using the pulmonary vein catheter of FIGS. 5A and 5B, a composition may be delivered to the lung via the lumen (12) that is in communication with the port (13) located on the distal end of the catheter, and may be collected via the lumen (16) of the deployable arm (i.e., the second catheter) that is in communication with the port (17) located on the distal end of the second catheter.

Although the catheter of FIGS. 5A and 5B has two lumens, it is understood that the catheter need only have one lumen (14) through which the deployable arm (i.e., the second catheter) is advanced. Likewise, the second catheter need not have a lumen.

In the case of individuals having, for example, more than two right pulmonary veins draining the right lung, the pulmonary vein catheter consisting of only one catheter employed will have two or more deployable arms (i.e., two or more catheters that may be deployed by being advanced through two or more lumens of the pulmonary vein catheter), where the distal end of the catheter is positioned in one of the right pulmonary veins, and each of the deployable arms is positioned in a remaining right pulmonary vein, such that all the right pulmonary veins of the individual have positioned in them either a distal end of the pulmonary vein catheter or a distal end of a deployable arm of the pulmonary vein catheter.

C) Lung-Specific Composition Delivery

For lung-specific delivery, a composition may be delivered to the lung via a pulmonary artery catheter, and collected via a pulmonary vein catheter, or vice-versa, where the pulmonary artery and vein supply and drain the same lung. Preferably, the lumen of the pulmonary vein catheter is connected to the lumen of the pulmonary artery catheter such that a composition exiting the lung and collected by the pulmonary vein catheter can be re-introduced into the lung via the pulmonary artery catheter, and a composition exiting the lung and collected by the pulmonary artery catheter can be re-introduced into the lung via the pulmonary vein catheter.

Preferably, at least one of the pulmonary vein catheter and the pulmonary artery catheter is positioned via a percutaneous route into the pulmonary veins and pulmonary artery, respectively, draining the administered lung.

In addition, a composition may be administered to a lung using only a pulmonary vein catheter, such as a pulmonary vein catheter consisting of two of more catheters, or a pulmonary vein catheter consisting of only one catheter and having two lumens. In the situation in which a pulmonary vein catheter consisting of two or more catheters (e.g., the catheter shown on FIG. 4) is used to deliver a composition to the lung, the lumens of the two or more catheters of the pulmonary vein catheter are preferably connected such that a composition delivered by one catheter of the pulmonary vein catheter may be retrieved by a second catheter of the pulmonary vein catheter. In the situation in which a pulmonary vein catheter consisting of only one catheter is used (e.g., the catheter shown on FIGS. 5A and 5B), the lumen of the deployable arm (ie., lumen (16) of FIG. 5B) and lumen of the distal end of the pulmonary vein catheter consisting of only one catheter (i.e., lumen (12) of FIGS. 5A and 5B) are connected such that a composition delivered by the distal end of the catheter may be retrieved by the catheter's deployable arm, and vice-versa.

Preferably, where a composition is administered to a lung using only a pulmonary vein catheter, the pulmonary artery supplying the administered lung is occluded with a pulmonary artery catheter having a deployable occluding device that is deployed to prevent leakage of the administered composition into the heart via the pulmonary artery.

The ex vivo connection of the lumens of the catheters of the invention allows for the recirculation of a composition being administered to an isolated lung. Such recirculation allows for longer exposure of the lung to the administered composition, a means for maintaining sterility of the composition, as well as the conservation of the composition (e.g., a therapeutic drug) and the delivery medium (e.g., blood or a physiologic solution). In addition, should the targeted lung be isolated for a prolonged period of time, the composition is preferably administered in a solution capable of carrying oxygen (e.g., blood) which can be oxygenated ex vivo according to standard cardiopulmonary bypass techniques.

D) Catheter specifications and modifications

The catheters of the invention may be modified such that each catheter can preferably be introduced over a guidewire and/or via a conventional introducer sheathe. In addition, preferably each catheter is also partially radio-opaque to facilitate fluoroscopic guidance of catheter placement. The catheters described above are designed to carry fluids at sufficient flow rates to facilitate efficient composition delivery, including, without limitation, flow rates of between 100–5000 mL/min., preferably flow rates of between 250–3000 mL/min., and most preferably, flow rates of between 500–2500 mL/min.

The catheters may be connected in circuits and combined with a pumping apparatus to allow uninterrupted flow of the composition as it enters, travels through, exits, and is re-introduced back into the lung. The catheters may be further equipped with gauges for monitoring pressure, thereby allowing an appropriate regulation of the pressure within the lung. Likewise, the catheters may be further equipped with flow meters for monitoring flow rates, thereby allowing an appropriate regulation of the flow rate of a composition being delivered to the lung.

The catheters employed in the invention are of variable diameter and length depending upon the age, health, and gender of the individual being administered the composition, as well as the route of catheter placement.

A Non-Surgical Percutaneous Approach

The invention allows complete percutaneous, minimally invasive, non-surgical isolation of the lung to facilitate delivery of a composition. Since a percutaneous approach is less invasive than surgical pulmonary artery access, ill patients have a greater tolerance for the procedure, a much faster recovery period with less associated morbidity and mortality, and fewer complications. True percutaneous isolation is significantly more effective at reducing the amount of composition "leaked" into the systemic circulation than either non-specific delivery or filtration, since the latter not only cannot be applied to all compositions, but is also limited with regard to filtration efficiency. With the improved isolation of composition delivery to the lung from systemic exposure that is provided by the invention, higher composition doses can be safely delivered to the lung, and pressurized delivery (see, e.g., Mann et al., PCT Publication No. WO98/20109) can be exploited to enhance composition delivery and uptake for an improved therapeutic effect with fewer deleterious side effects and reduced morbidity.

Percutaneous approaches are well known to the ordinarily skilled physician, and are generally described in Brown et al., Heart 79: 24–28, 1998; Kinoshita et al., Br. Heart J. 69(4): 322–326, 1993; Feldman et al., Cathet. Cardiovasc. Diagn. suppl 2: 26–34, 1994; Moore et al., Am. Heart J. 130(6): 1245–1249, 1995. To achieve a non-surgical, percutaneous approach for delivery of a catheter to the pulmonary artery or the pulmonary veins of the lung, an intravenous or intra-arterial approach may be employed. The intravenous/intra-arterial approach preferably uses guidewire techniques and is under the guidance of ultrasound imaging (e.g., two-dimensional or Doppler flow imaging), radiographic imaging (e.g., fluoroscopy or computed tomography), or magnetic resonance imaging. Catheter exchanges using conventional techniques may then be performed for the placement of the catheter into the left or right pulmonary veins or arteries using this venous/arterial access technique. These approaches are discussed below.

A) An intravenous approach

The intravenous approach for the placement of the pulmonary artery catheter involves the direct puncture of a large vein, preferably the jugular, subclavian, or femoral vein. The catheter is then advanced through the vena cava, into the right atrium, across the tricuspid valve, into the right ventricle, across the pulmonary valve, into the pulmonary trunk, and then into the left or right pulmonary artery. This puncture and catheter placement is preferably achieved with the guidance of an imaging modality, including, without limitation, ultrasound (e.g., two-dimensional or Doppler flow imaging), radiographic imaging (e.g., fluoroscopy or computed tomography), or magnetic resonance imaging. Conventional percutaneous access techniques such as guidewire manipulations and introducer sheathe insertions may then be utilized for the placement of the catheter into the left or right pulmonary artery for movement into the appropriate position for delivery or retrieval of a composition.

B) An intra-arterial approach

The intra-arterial approach for the placement of the pulmonary vein catheter involves the direct puncture of a large artery, preferably by the carotid, subclavian, or femoral artery. The catheter is then advanced through the aorta, across the aortic valve, into the left ventricle, across the mitral valve, into the left atrium, and into the left or right pulmonary veins.

Retrograde Flow

The invention described herein allows for a manipulation of the direction of flow utilized in the delivery of a composition to the lung. In vivo, blood flow through the lung proceeds from entry into the lung through the pulmonary artery to departure from the lung through the pulmonary veins. By utilizing the methods of the invention, administration of a composition to the lung in a retrograde fashion is allowed. This technique may serve to deliver the administered composition to hard-to-reach areas of the lung. For example, a composition may be administered via the pulmonary vein catheter, allowed to flow through the lung in a direction opposite to that taken by normal blood, and collected as it exits the lung via the pulmonary artery catheter. The exiting composition may then be re-introduced into the lung via the pulmonary vein catheter, as discussed above.

Timed Exposure

The quantity of blood in the lungs can vary, under different physiological and pathological conditions, to as little as 50% of normal up to as high as 200% of normal. Given this capacity of the lung to serve as a blood reservoir, the invention allows for timed exposure of a targeted, isolated lung to an administered composition.

For example, either the pulmonary vein catheter or the pulmonary artery catheter may be employed for administration of a composition. Preferably, both the pulmonary artery and the pulmonary vein catheters have occluding devices to prevent leakage of the composition into the heart. A composition may thus be administered to the isolated lung, allowing the composition to distend the lung (but not to the point of damage). The administered composition may then be allowed to remain in the lung for a desired period of time. For example, the administered composition may be allowed to remain in the lung for a prolonged period of time, or may be immediately drained from the lung. Duration of exposure of the lung to the composition will vary depending upon the composition administered, the concentration of the composition, and the type of lung disease being treated.

Drainage of a composition delivered to the lung by this approach is achieved at any desired time-point by flushing either the pulmonary artery catheter or the pulmonary vein catheter with any suitable fluid, such as physiological sterile saline. If desired, the composition draining the lung may be collected, and possibly subsequently re-introduced into the lung. The deployable occluding devices (e.g., balloons) of the catheters may then be deflated, and the catheters removed, thereby restoring normal blood flow to the targeted lung.

Compositions

The composition delivered to the lung using the method and apparatus of the invention may be any solution or suspension of a compound in a fluid. Methods well known in the art for making formulations are found, for example, in *Remington's Pharmaceutical Sciences* ($18^{th}$ edition), ed. A. Gennaro, 1990, Mack Publishing Company, Easton, Pa. Exemplary fluids include, without limitation, sterile water, physiological saline, or blood. If one of the right or left lung is isolated for prolonged periods of time, an oxygen-carrying solution, such as blood, is preferably employed. In approaches in which the lung is isolated, and a composition is administered to the lung, allowed to passed through the lung, and then allowed to exit the lung, the composition is preferably in an oxygen-carrying solution which may be oxygenated while in transit ex vivo between the various catheters of the apparatus. Compositions of the invention include, without limitation, contrast agents; drugs, such as chemotherapeutic agents and antibiotics; and suspensions of cells. In addition, although by no means limiting, the *Physician's Desk Reference* (Medical Economics Co. Inc. Montvale, N.J., 1998) provides details about the preferred dosage and indications of a variety of therapeutic compounds and compositions which may be useful in treating diseases of the lung.

The following examples are to illustrate the invention. They are not meant to limit the invention in any way.

EXAMPLE I

A Method for Treating Primary Cancer of the Lung

A patient with a primary cancer of the lung, including, without limitation, squamous cell carcinoma, adenocarcinoma, large cell undifferentiated carcinoma, small cell carcinoma, and bronchiolalveolar tumors, may be treated with the methods provided herein. Although in this example, the treatment of only one of the two lungs is described, if the cancer has spread to both lungs, both lungs may be treated sequentially (i.e., a composition is first administered to the right lung, and then is administered to the left lung) or simultaneously.

In this example of a method to treat a patient with small cell carcinoma in only the right lung, the right lung of the patient is drained by two right pulmonary veins. A balloon catheter having an inflated balloon diameter of between 1.0 cm. and 3.0 cm. and a lumen that is in communication with a port located distal to the balloon is inserted into the pulmonary artery using a percutaneous approach. The pulmonary artery catheter used in this example is similar to that depicted on FIG. 3. Such a catheter is commercially available from, for example, Boston Scientific Corp. (Natick, Mass.).

The pulmonary artery catheter is placed via a percutaneous approach into the right pulmonary artery using fluoroscopic guidance. The catheter is introduced into the superior vena cava, and the balloon is inflated. The catheter is advanced with the flow of blood into the right atrium, across the tricuspid valve, and into the right ventricle. The catheter is then advanced across the pulmonary valve, into the pulmonary trunk, and into the right pulmonary artery. Correct placement of the catheter into the right pulmonary artery (versus the left pulmonary artery) is verified fluoroscopically. The passage of the catheter through the various compartments can be monitored via connection of a distal port in the tip of the catheter to a pressure transduction device for measurement of pressure waveforms in the different compartments, including the occluded pulmonary artery. Similar catheter placement procedures are well known (see, for example, Blake et al., U.S. Pat. No. 3,995,623).

A pulmonary vein balloon catheter, consisting of one catheter (such as the catheter depicted in FIGS. 5A and 5B) and having an inflated balloon diameter of between 0.5 cm. and 4.0 cm., is placed into the right pulmonary veins using a percutaneous approach. In this approach, the catheter is passed over a guidewire into the aorta, across the aortic valve, into the left ventricle, across the mitral valve, and into the left atrium to the point where the right pulmonary veins join the left atrium. The pulmonary vein balloon catheter has a deployable arm (i.e., a second catheter) that may be deployed through a lumen of the pulmonary vein catheter to exit the lumen via a port or valve located proximal to the deployable balloon of the pulmonary vein catheter.

The distal end of the pulmonary vein catheter is first advanced into one of the two right pulmonary veins. Through external control, the deployable balloon of the distal end of the catheter is inflated, firmly lodging the catheter in one of the two right pulmonary veins. Next, the deployable arm is deployed by advancing a second catheter through a lumen of the pulmonary vein catheter that is in communication with a port located proximal to the deployable balloon of the catheter. When deployed, the deployable arm (i.e., the second catheter) has a deployable balloon and a lumen that is in communication with a port located distal to the deployable balloon of the deployable arm. The deployable arm, again under fluoroscopic guidance, is positioned into the second of the two right pulmonary veins. The deployable balloon of the deployed deployable arm is then inflated, firmly lodging the second catheter into the second of the two right pulmonary veins. Hence, both right pulmonary veins are occluded.

An amount of cisplatin that is useful for treating lung cancer (e.g., 20–80 mg/m$^2$) is mixed with an amount of blood sufficient to completely saturate the lung (e.g., 250 mL). Most preferably, the blood is from the patient; less preferably, the blood is from a cross-matched donor. The blood/cisplatin composition is added to the right lung via the pulmonary artery catheter. The pulmonary artery catheter is connected to the pulmonary vein catheter such that a composition delivered to the right lung by the pulmonary artery catheter is collected by the pulmonary vein catheter and returned to the right lung via the pulmonary artery catheter.

The blood/cisplatin composition is allowed to recirculate through the right lung via the pulmonary artery and pulmonary vein catheters for several hours. As the blood/cisplatin circulates ex vivo between the pulmonary artery and pulmonary vein catheters, the blood cells are preferably oxygenated, as during standard cardiopulmonary bypass surgery.

Following treatment, the pulmonary vein catheter is disconnected from the pulmonary artery catheter. The pulmonary artery catheter is then flooded with sterile saline, and the effluent blood/cisplatin composition is collected by the pulmonary vein catheter and may be either saved or discarded. To remove the pulmonary artery catheter, the balloon of the pulmonary artery catheter is deflated, and the pulmonary artery catheter is removed. To remove the pulmonary vein catheter, the balloon of the deployable arm of the pulmonary vein catheter (i.e., the second catheter) is first deflated, and the deployable arm retrieved to return the pulmonary vein catheter to the position as diagramed in FIG. 5A. Next, the deployable balloon of the pulmonary vein catheter is deflated, and the pulmonary vein catheter is removed.

The cisplatin treatment is repeated as necessary to reduce the number of cancerous cells in the right lung and/or to alleviate the patient's symptoms.

EXAMPLE II

A Method for Treating Pulmonary Aspergillosis

Pulmonary aspergillosis is an opportunistic infection of the lung. Since this disease may involve only a single lung, it is an ideal disease candidate for treatment using the methods and apparati of the present invention.

Figure 4:
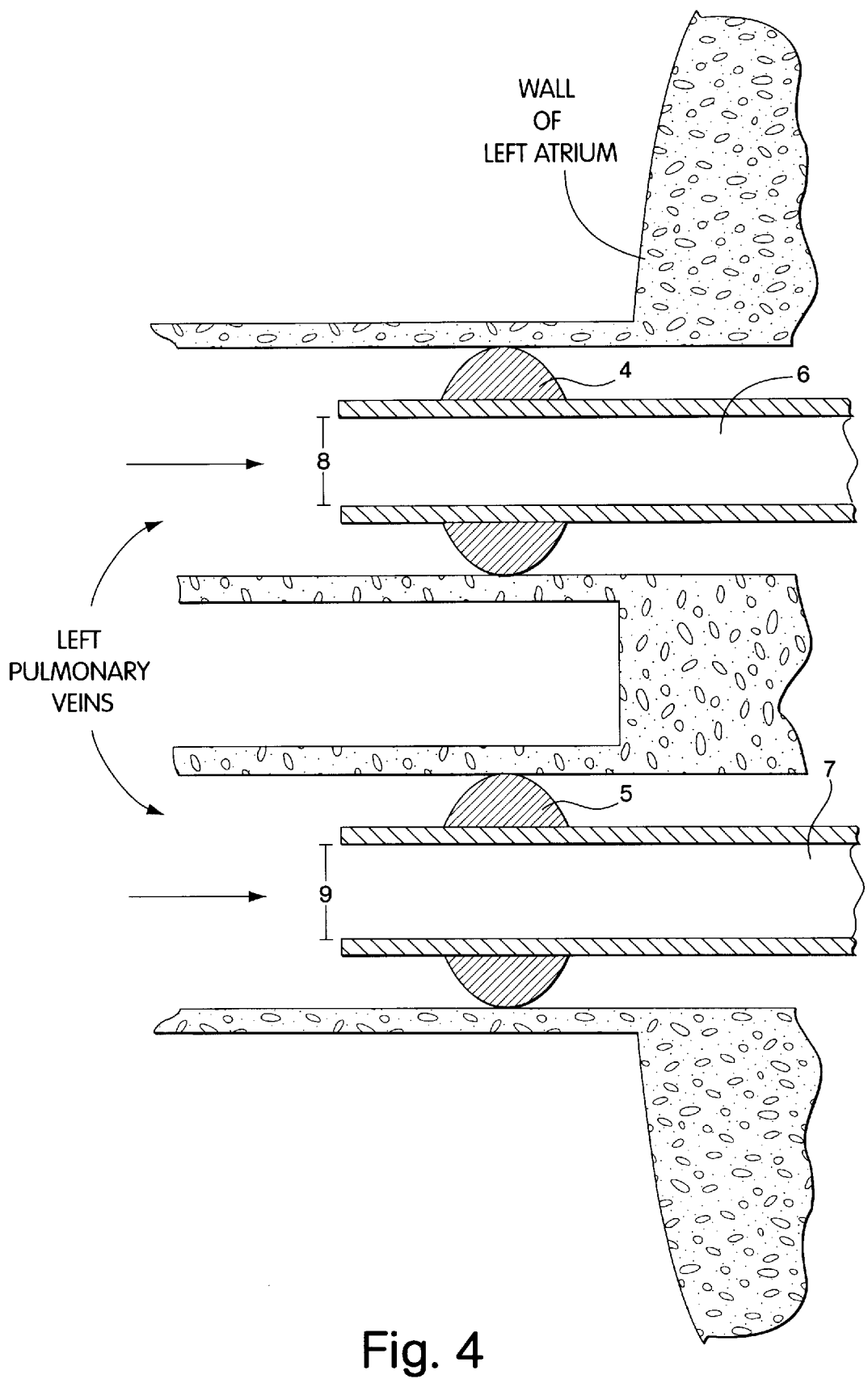
FIG. 4 is a schematic representation of a horizontal cross section of a pulmonary vein catheter consisting of two catheters, each of which is introduced into one of two pulmonary veins draining the same lung. In this figure, the pulmonary veins are draining the left lung. Note that the deployable occluding devices of each of the catheters (4 and 5), denoted as hatched sections, are in the deployed position, thus firmly lodging the catheters against the walls of the left pulmonary veins. Direction of the flow of blood in the pulmonary veins is depicted with arrows.

In this example, aspergillosis affecting the left lung is treated with an antifungal agent, such as amphotericin B, using the methods of the invention. The left lung of the patient in this example is drained by two pulmonary veins. Employing computed tomography guidance and a standard guidewire technique (using a guidewire commercially available from, e.g., Microvena, White Bear Lake, Minn.), a pulmonary artery catheter with an inflated balloon diameter of between 1.0 cm. and 3.0 cm., is inserted into the right pulmonary artery of a patient using an intravenous approach through entry into the femoral vein. Such a catheter is commercially available from, e.g., Meditech, Watertown, Mass., and has a deployable balloon. A pulmonary vein catheter consisting of two catheters, such as the pulmonary vein catheter shown on FIG. 4, is placed into the left pulmonary veins using an intra-arterial approach through the aorta, again, employing computed tomography guidance and standard guidewire techniques. Each of the catheters of the pulmonary vein catheter has a lumen that is in communication with a port located distal to a deployable balloon, and each catheter is of a diameter suitable for insertion into a left pulmonary vein (e.g., an inflated balloon diameter of between 0.5 cm. and 4.0 cm.).

The balloons on the pulmonary artery catheter and the pulmonary vein catheters are deployed, firmly lodging the catheters in the left pulmonary artery and left pulmonary veins. Sterile saline is administered via one or both of the pulmonary vein catheters and blood is evacuated through the pulmonary artery catheter. Blood collected by the pulmonary artery catheter may be returned to the patient via the jugular vein, or other intravenous access.

An amount of amphotericin B (commercially available from Sequus Pharmaceuticals, Menlo Park, Calif.) useful for treating aspergillosis of the lung (e.g., 3–30 mg/kg) is then administered through the pulmonary vein catheters and allowed to incubate in the lung for an hour. The lumen of the pulmonary artery catheter may be occluded at this time to facilitate the elevation of pressure during infusion of the amphotericin B solution. Sterile saline is then administered via one or both of the pulmonary vein catheters to flush the antifungal solution from the lung via the pulmonary artery catheter. Next, the balloons of all catheters (i.e., the balloons of both catheters of the pulmonary vein catheter and the balloon of the pulmonary artery catheter) are deflated, and the catheters are removed.

If required, the dose of amphotericin B may be divided into daily doses and the delivery procedure carried out on a repeated basis. It will be understood, of course, that the size of the catheters and the dosage of antifungal agent used will vary in accordance with the patient (e.g., smaller catheters are used on a child).

EXAMPLE III

A Method for Treating Metastatic Lung Cancer

In situations where cancerous growths are apparent in a lung, but the possibility exists that metastatic particles may be lodged elsewhere in the body, it may be advisable to administer a composition (e.g., a chemotherapeutic agent) directly to the most severely affected lung, and then to allow the composition to diffuse throughout the rest of the body. In this situation, a catheter, such as the catheter depicted on FIG. 3, is inserted into the pulmonary artery supplying blood to the most severely affected lung (i.e., the right or left pulmonary artery) via an intravenous approach through entry into the vena cava. Such a catheter has a deployable occluding balloon and a lumen that is in communication with a port located distal to the balloon, and may be commercially available from, for example, Advanced Cardiovascular Systems (Santa Clara, Calif.), Cordis Corp. (Miami, Fla.), or Medtronic Inc. (Minneapolis, Minn.).

Depending upon the type of cancer being treated, a chemotherapeutic reagent is administered to the affected lung at a dosage sufficient to slow, stop, or reverse the growth of the cancer. For example, chemotherapeutic agents including, without limitation, carmustine, mechlorethamine, bleomycin, mitomycin cytarabine, doxorubicin, fludarabine, ifosfamide, methotrexate, dacarbazine, mitoxantrone, pentostatin, daunorubicin, vinblastine, cladribine, and vincristine, may be administered at an effective dosage to an affected lung via a pulmonary artery catheter. Such dosages may be determined with guidance from various medical references (e.g., the *Physician's Desk Reference,* Medical Economics Co. Inc. Montvale, N.J., 1998), and manufacturers' specifications for each chemotherapeutic reagent.

Once the pulmonary artery catheter is positioned in the artery supplying blood to the affected lung, the deployable balloon is inflated, thereby blocking blood flow into the affected lung. The composition is then administered to the lung to displace the blood in the lung, where the displaced blood is simply pushed into the left atrium of the heart. Since there is no blood flowing through the affected lung, composition flow through the lung may then be paused, allowing the composition (i.e., the chemotherapeutic agent) to remain in the lung for an desired period of time. Should the patient, in this time period, require externally oxygenated blood (due to the non-functioning of the affected lung), blood may be oxygenated ex vivo via catheters positioned in the femoral artery and femoral vein according to standard cardiopulmonary bypass surgery techniques.

Although flow of the composition in the pulmonary artery catheter is halted once the composition has displaced the blood contained within the affected lung, some of the composition may leak into the pulmonary veins draining the affected lung, and, hence, may leak into the heart, aorta, and surrounding tissue. However, because the leaking composition is diluted by blood flowing into the heart from the lung not being administered the composition, the concentration of the composition will be lessened as the composition is carried by the blood to other parts of the body. To maintain this dilution of the composition as it reaches the remainder of the body, once the desired period of time has passed for allowing the composition to remain, without flow, in the affected lung, blood is slowly added to the affected lung via the pulmonary artery catheter, thus slowly mixing with and displacing the composition in the affected lung. Hence, the composition reaching the rest of the body will be in a concentration that is less detrimental to non-cancerous cells. Conversely, since the composition is administered to the rest of the body, albeit at a reduced concentration, the composition is able to affect the growth of any cancerous cells that may have metastasized from the cancer in the affected lung.

Once most of the composition is removed from the affected lung, the balloon of the catheter is deflated, and the catheter removed. If both lungs are affected by the cancer, the other lung may be similarly treated, either immediately or at another time. Subsequent treatments of the affected lung with the same or different chemotherapeutic reagents are repeated as necessary to reduce, or at least alleviate the symptoms of, metastatic lung cancer.

EXAMPLE IV

A Method for Treating Metastatic Lung Cancer in Both Lungs

In the situation in which a metastatic lung cancer has spread to both lungs of a patient, both lungs may be treated simultaneously with a chemotherapeutic agent. In this example, the patient has two pulmonary veins draining each lung. To achieve simultaneous administration of a composition to both lungs, cardiopulmonary bypass must first be established via, for example, canulation of the femoral artery and vein. Blood is collected from the femoral vein and oxygenated ex vivo according to standard cardiopulmonary bypass techniques. Oxygenated blood in then re-infused into the patient via the femoral artery.

Once cardiopulmonary bypass is established, the heart is temporarily arrested via infusion of a cardioplegic solution into the coronary circulation using, for example, a percutaneous aortic root infusion balloon catheter. Thereupon, a pulmonary artery catheter is placed via a percutaneous approach into the main pulmonary artery trunk using fluoroscopic guidance. For example, the balloon catheter is introduced into the inferior vena cava and advanced into the right atrium, across the tricuspid valve, and into the right ventricle. The catheter is then advanced across the pulmonary valve and into the main pulmonary artery trunk, where the balloon of the catheter is inflated to completely occlude the pulmonary trunk.

Prior to the placement of the coronary infusion catheter and inflation of the aortic root balloon, balloon catheters are positioned into all of the pulmonary veins draining both the right and left lungs. Preferably, two pulmonary vein catheters, each with a deployable arm, are employed to minimize the number of catheters being inserted into the aorta, across the aortic valve, into the left ventricle, across the mitral valve, into the left atrium, and into the pulmonary veins. Where two pulmonary vein catheters, each with a deployable arm, are employed, and where the distal end of each of the two catheters is positioned in a left or right pulmonary vein, the deployable arm of each of the catheters is next positioned into the remaining left or right pulmonary vein such that its inflatable balloon can occlude the remaining left or right pulmonary vein. All the pulmonary veins draining the left and lungs are thus occluded.

Following evacuation of blood from the lungs by flushing a suitable fluid (e.g., sterile saline) through either the pulmonary trunk catheter or the pulmonary vein catheters, a chemotherapeutic agent-containing solution is infused into both lungs and allowed to incubate for a desired amount of time. If the incubation time is of prolonged duration, recirculation of the chemotherapeutic solution may be desired, where the solution is capable of bearing oxygen (e.g., the solution is a desired amount of the chemotherapeutic agent dissolved in blood), to avoid hypoxia of the lung cells. In the recirculation method, the solution is oxygenated ex vivo, and, preferably, the catheters are connected to one another such that the solution exiting, for example, the pulmonary vein catheters is re-introduced via the pulmonary trunk catheter.

Following incubation of the lungs for the desired amount of time with the chemotherapeutic solution, the solution is flushed from the lungs by infusing either the pulmonary trunk catheter or the pulmonary vein catheters with sterile saline (or other fluid, such as blood). During the flushing of the solution from the lungs, the catheters are, of course, disconnected from one another. Next, the balloons of all catheters (including those of the deployable arms of the pulmonary vein catheters) are deflated, and the catheters removed. Normal coronary blood flow is reestablished and beating of the heart is allowed to resume, facilitated, if necessary, by the application of standard resuscitation techniques (e.g., electrical defibrillation). Finally, the canulas are removed from the femoral artery and femoral vein, as control of circulation is restored to the heart.

As in the above examples, repeated treatment with the same or different chemotherapeutic agent may be employed to force the metastatic lung cancer into remission. If, for example, cancerous growths remain in only one lung, the affected lung may be treated in isolation, thereby retaining a functional heart to control circulation in conjunction with the non-treated lung.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A method for delivering a composition to a lung, said method comprising the steps of:
    (a) inserting a pulmonary artery catheter into a pulmonary artery supplying said lung via a first non-surgical percutaneous route, wherein said pulmonary artery catheter comprises a deployable means for occluding said inserted pulmonary artery;
    (b) inserting a pulmonary vein catheter into a pulmonary vein draining said lung via a second non-surgical percutaneous route, wherein said pulmonary vein catheter comprises a deployable means for occluding said inserted pulmonary vein; and
    (c) delivering said composition to said lung via at least one of the group consisting of said pulmonary artery catheter and said pulmonary vein catheter.

2. The method of claim 1, wherein said lung comprises two or more pulmonary veins that drain said lung.

3. The method of claim 2, wherein step (b) further comprises inserting a pulmonary vein catheter into each of said pulmonary veins draining said lung, wherein each of said pulmonary vein catheters comprises a deployable means for occluding the pulmonary vein into which it is inserted, the number of pulmonary vein catheters is equal to the number of pulmonary veins draining said lung, and not more than one of said pulmonary vein catheters is inserted into one pulmonary vein.

4. The method of claim 2, wherein said pulmonary vein catheter further comprises a number of deployable arms that is equal to the number of pulmonary veins draining said lung minus one.

5. The method of claim 4, wherein step (b) further comprises inserting said deployable arms of said pulmonary vein catheter into said number of pulmonary veins draining said lung minus one, wherein each of said deployable arms, when deployed, comprises a deployable means for occluding the pulmonary vein into which it is inserted, and not more than one of said deployable arms is inserted into one pulmonary vein.

6. The method of claim 5, wherein said delivery step is via at least one of the group consisting of said pulmonary artery catheter, said pulmonary vein catheter, and at least one of said deployable arms of said pulmonary vein catheter.

7. The method of claim 6, wherein said composition delivered to said lung is collected by at least one of the group consisting of said pulmonary artery catheter, said pulmonary vein catheter, and at least one of said deployable arms of said pulmonary vein catheter, wherein said delivering catheter and said collecting catheter are different.

8. The method of claim 7, wherein said delivery catheter is connected to said collecting catheter, whereby said composition collected by said collecting catheter is returned to said lung by said delivering catheter.

9. The method of claim 3, wherein said delivering step is via at least one of the group consisting of said pulmonary artery catheter and at least one of said pulmonary vein catheters.

10. The method of claim 7, wherein said composition delivered to said lung is collected by at least one of the group consisting of said pulmonary artery catheter and at least one of said pulmonary vein catheters, wherein said delivering catheter and said collecting catheter are different.

11. The method of claim 10, wherein said delivering catheter is connected to said collecting catheter, whereby said composition collected by said collecting catheter is returned to said lung by said delivering catheter.

12. The method of claim 1, wherein said composition delivered to said lung is collected by at least one of the group consisting of said pulmonary artery catheter and said pulmonary vein catheter, wherein said delivering catheter and said collecting catheter are different.

13. The method of claim 12, wherein said delivering catheter is connected to said collecting catheter, whereby said composition collected by said collecting catheter is returned to said lung by said delivering catheter.

14. The method of claim 1, wherein at least one of said pulmonary artery catheter and said pulmonary vein catheter is adapted for insertion via a conventional introducer sheathe.

15. The method of claim 1, wherein at least one of said pulmonary artery catheter and said pulmonary vein catheter is adapted for insertion over a guidewire.

16. The method of claim 1, wherein at least one of said pulmonary artery catheter and said pulmonary vein catheter is equipped with a gauge for monitoring pressure.

17. The method of claim 1, wherein at least one of said pulmonary artery catheter and said pulmonary vein catheter is equipped with a flow meter for monitoring flow rate.

18. The method of claim 1, wherein at least one of said pulmonary artery catheter and said pulmonary vein catheter is at least in part radio-opaque.

19. The method of claim 1, wherein at least one of said pulmonary artery catheter and said pulmonary vein catheter further comprises a lumen that is in communication with a port located distal to said deployable occluding means.

20. The method of claim 1, wherein at least one of said first non-surgical percutaneous route and said second non-surgical percutaneous route is visualized by a guidance technique selected from the group consisting of ultrasound guidance, radiographic guidance, and magnetic resonance guidance.

21. The method of claim 1, wherein said first non-surgical percutaneous route is an intravenous approach.

22. The method of claim 1, wherein said second non-surgical percutaneous route is an intra-arterial approach.

23. The method of claim 1, wherein, said composition is delivered to said lung via said pulmonary vein catheter and is collected from said lung via said pulmonary artery catheter.

24. A method for delivering a drug to a lung comprising more than one pulmonary vein, said method comprising the steps of:

(a) inserting a pulmonary vein catheter into a pulmonary vein of said lung via a non-surgical percutaneous route, wherein said pulmonary vein catheter comprises (i) a deployable means for occluding the pulmonary vein into which it has been inserted, and (ii) a number of deployable arms that is equal to the number of pulmonary veins of said lung minus one;

(b) inserting each of said deployable arms into a different pulmonary vein of said lung, wherein the pulmonary vein into which a deployable arm is inserted does not contain said pulmonary vein catheter; and (b) delivering said drug to said lung via said pulmonary vein catheter and said deployable arms.

25. The method of claim 24, wherein said non-surgical percutaneous route is visualized by a guidance technique selected from the group consisting of ultrasound guidance, radiographic guidance, and magnetic resonance guidance.

26. The method of claim 24, wherein said non-surgical percutaneous route is an intravenous approach.

27. The method of claim 24, wherein said pulmonary vein catheter is adapted for insertion via a conventional introducer sheathe.

28. The method of claim 24, wherein said pulmonary vein catheter is adapted for insertion over a guidewire.

29. The method of claim 24, wherein said pulmonary vein catheter is equipped with a gauge for monitoring pressure.

30. The method of claim 24, wherein said pulmonary vein catheter is equipped with a flow meter for monitoring flow rate.

31. The method of claim 24, wherein said pulmonary vein catheter is at least in part radio-opaque.

32. The method of claim 24, wherein said pulmonary vein catheter further comprises a lumen that is in communication with a port located distal to said deployable occluding means.

33. A method for delivering a drug to a lung comprising more than one pulmonary vein, said method comprising the steps of:

(a) inserting a pulmonary vein catheter into each pulmonary vein of said lung via a non-surgical percutaneous route, wherein each pulmonary vein catheter comprises a deployable means for occluding the pulmonary vein into which it has been inserted and not more than one catheter is inserted into a single pulmonary vein; and (b) delivering said drug to said lung via the pulmonary vein catheters.

34. The method of claim 33, wherein said non-surgical percutaneous route is visualized by a guidance technique selected from the group consisting of ultrasound guidance, radiographic guidance, and magnetic resonance guidance.

35. The method of claim 33, wherein said non-surgical percutaneous route is intravenous.

36. The method of claim 33, wherein said pulmonary vein catheter is adapted for vein insertion via a conventional introducer sheathe.

37. The method of claim 33, wherein said pulmonary vein catheter is adapted for insertion over a guidewire.

38. The method of claim 33, wherein said pulmonary vein catheter is equipped with a gauge for monitoring pressure.

39. The method of claim 33, wherein said pulmonary vein catheter is equipped with a flow meter for monitoring flow rate.

40. The method of claim 33, wherein said pulmonary vein catheter is at least in part radio-opaque.

41. The method of claim 33, wherein said pulmonary vein catheter further comprises a lumen that is in communication with a port located distal to said deployable occluding means.

* * * * *

UNITED STATES PATENT AND TRADEMARK OFFICE
CERTIFICATE OF CORRECTION

PATENT NO. : 6,077,256
DATED : June 20, 2000
INVENTOR(S) : Michael J. Mann

It is certified that error appears in the above-identified patent and that said Letters Patent is hereby corrected as shown below:

<u>Column 16,</u>
Line 49, "left and lungs" should be changed to -- left and right lungs --

<u>Column 19,</u>
Line 24, change the last step from "(b)" to -- (c) --.

Signed and Sealed this

Eleventh Day of February, 2003

JAMES E. ROGAN
*Director of the United States Patent and Trademark Office*